US012332249B1

(12) United States Patent
Alazemi et al.

(10) Patent No.: US 12,332,249 B1
(45) Date of Patent: Jun. 17, 2025

(54) BIOMOLECULE DETECTION METHOD USING DIFFUSION ORDERED SPECTROSCOPY

(71) Applicant: KUWAIT UNIVERSITY, Safat (KW)

(72) Inventors: Abdulrahman Miteb Alazemi, Safat (KW); Fouzi Mouffouk, Safat (KW); Laila Abdulmohsen Alhaddad, Safat (KW); Abdulhamid Mohammed Emwas, Thuwal (SA); Mohamed Khaled Emira, Safat (KW); Tasneem Salem Habib, Safat (KW)

(73) Assignee: KUWAIT UNIVERSITY, Safat (KW)

( * ) Notice: Subject to any disclaimer, the term of this patent is extended or adjusted under 35 U.S.C. 154(b) by 0 days.

(21) Appl. No.: 18/923,470

(22) Filed: Oct. 22, 2024

(51) Int. Cl.
*G01N 33/532* (2006.01)
*G01N 33/558* (2006.01)
*G01N 33/58* (2006.01)
*G01N 33/68* (2006.01)

(52) U.S. Cl.
CPC ....... *G01N 33/6845* (2013.01); *G01N 33/582* (2013.01)

(58) Field of Classification Search
CPC ............. G01N 33/6845; G01N 33/582; G01N 33/532; G01N 33/5375; G01N 33/558; B01L 2400/0472
See application file for complete search history.

(56) References Cited

PUBLICATIONS

Mosbach et al. Modulation of the diffusion coefficient of a hapten-modified redox species as a basis for an amplified electrochemical affinity assay. Sensors and Actuators B 70 (2000), pp. 145-152 (Year: 2000).*
Bewley et al. Characterizing carbohydrate-protein interactions by NMR. Biopolymers. Oct. 2013 ; 99(10), pp. 1-18. (Year: 2013).*
Xu, Chenglong, et al. "19F DOSY diffusion-NMR spectroscopy of fluoropolymers." Magnetic Resonance in Chemistry 55.5 (2017): 472-484.
Giubertoni, Giulia, et al. "Multidimensional infrared diffusion-ordered spectroscopy in depletion mode distinguishes protein amyloids and monomers." The Journal of Chemical Physics 158.12 (2023).
Simpson, Andre J. "Determining the molecular weight, aggregation, structures and interactions of natural organic matter using diffusion ordered spectroscopy." Magnetic Resonance in Chemistry 40.13 (2002): S72-S82.
Groves, Patrick, et al. "Protein molecular weight standards can compensate systematic errors in diffusion-ordered spectroscopy." Analytical biochemistry 331.2 (2004): 395-397.
Ramanujam, Venkatraman, et al. "Protein structural changes characterized by high-pressure, pulsed field gradient diffusion NMR spectroscopy." Journal of Magnetic Resonance 312 (2020): 106701.
Kandiyal, Pancham S., et al. "Size determination of protein oligomers/aggregates using diffusion NMR spectroscopy." Protein Self-Assembly: Methods and Protocols (2019): 173-183.

* cited by examiner

*Primary Examiner* — Shafiqul Haq
(74) *Attorney, Agent, or Firm* — Nath, Goldberg & Meyer; Joshua B. Goldberg (57) ABSTRACT

A method of detecting a second target protein in a sample can include preparing a tracer bound-first target protein; determining a diffusion coefficient for the tracer bound-first target protein before contacting the tracer bound-first target protein with a sample to obtain a first value; contacting the tracer bound-first target protein with a sample; determining a diffusion coefficient for the tracer bound-first target protein after contacting the sample to obtain a second value; and identifying a presence of the second target protein in the sample when a change in the diffusion coefficient values is determined.

6 Claims, 2 Drawing Sheets

BIOMOLECULE DETECTION METHOD USING DIFFUSION ORDERED SPECTROSCOPY

BACKGROUND

1. Field

The present disclosure relates to a method for detecting biomolecular interactions, using molecular tracers.

2. Description of the Related Art

Sensors are devices that can detect various physical inputs like light, pressure, heat, magnetism, sound, and motion. These inputs are then transformed into data that can be conveniently processed and understood. Sensors are available in different shapes and forms to cater to a wide range of applications, including temperature sensors in coffee makers, touch sensors in smart devices, motion sensors for controlling lights, as well as basic sensors for monitoring health and the environment.

In 1956, the first biosensor was invented by Professor Leland C. Clark for oxygen detection. The first commercial device was a glucose biosensor that was released in 1972 by the Yellow Spring company. A biosensor is the analytical device that combines the bioreceptor which detects the analyte with the physicochemical transducer to produce a measurable signal. High performance biosensors are selective, sensitive, stable, reproducible, productive, and able to generate corresponding restraint for a repetition experimental set-up.

Biosensors can be classified into three categories, optical, electrochemical or mass-based sensors according to either bioreceptor elements or transducer types. Optical biosensors are based on optical techniques such as fluorescence, luminescence, and surface plasmon resonance (SPR). Electrochemical biosensors may be categorized as amperometric, potentiometric or conductometric biosensors. Mass-based sensors detection mode relies on the measurement of the voltage across a piezoelectric unit that has been generated by the change in mass of the analyte. Other types of biosensors are magnetic sensors and thermal biosensors.

Detecting weakly expressed proteins and protein complexes in biological samples without purification or separation poses a significant challenge for biologists, as achieving an adequate signal-to-noise ratio is difficult.

Biosensor technology has become a major player in many applications ranging from military industries to the healthcare field. However, many challenges are facing these sectors such as detecting low-concentration protein complexes in biological samples or understanding protein properties interaction. Thus, new methods of detecting biomolecules which can be used for detecting weakly expressed biomolecules and detecting biomolecules in non-purified samples are desired.

SUMMARY

According to an embodiment, the present subject matter relates to a method for detecting biomolecules by calculating the diffusion rate using Diffusion Ordered Spectroscopy (DOSY) as a transducer. The method enables the detection of biomaterials such as proteins and DNA by measuring the rate of diffusion coefficient of two interacting biomolecules utilizing a tracer molecule including polyfluorine. In an embodiment, the tracer molecule comprises pentadecafluorooctanoyl. In an embodiment, the interacting biomolecules comprise biotin and avidin. In an embodiment, the tracer molecule includes a polyfluorene compound, such as pentadecafluorooctanoyl. In an embodiment, the diffusion coefficient rates of biotin-pentadecafluorooctanoyl and avidin-biotin-pentadecafluorooctanoyl complex calculated $1.937 \times 10^{-8}$ m$^2$/s and $1.12 \times 10^{-12}$ m$^2$/s respectively. The variations in diffusion rate can be attributed to the alterations in molecular weight and size, which align with the interaction between the tracer and the target molecule. Utilization of polyfluorine and analogous molecules as tracers can achieve precise and selective results without requiring use of a secondary antibody or additional purification steps.

In an embodiment, the present subject matter relates to a method for detecting a presence of a second target biomolecule in a sample including preparing a molecular tracer; binding the molecular tracer to first target biomolecule to provide a tracer bound-first target biomolecule; contacting the tracer-bound first target biomolecule with a sample to detect a presence of a second target biomolecule in the sample; determining a diffusion coefficient value for the tracer bound-first target protein before and after contacting the tracer bound-first target molecule with the sample; and detecting a presence of the second target biomolecule in the sample when a difference is determined between the diffusion coefficient values.

In another embodiment, the present subject matter relates to a method of binding a molecular tracer to a first target biomolecule. In an embodiment, the first target biomolecule is a protein. In an embodiment, the protein is biotin. In an embodiment, the method may include dissolving biotin hydrazide in tetrahydrofuran (THF) to obtain a reaction mixture, adding triethylamine to the reaction mixture to obtain a second reaction mixture, stirring the second reaction mixture, adding pentadecafluorooctanoyl chloride to the second reaction mixture under nitrogen gas to obtain a third reaction mixture, stirring the third reaction mixture, and removing the THF from the third reaction mixture under reduced pressure to obtain a fourth reaction mixture. The method may also include purifying the fourth reaction mixture.

According to an embodiment, a method of detecting a second target protein in a sample can include preparing a tracer bound-first target protein; determining a diffusion coefficient for the tracer bound-first target protein before contacting the tracer bound-first target protein with a sample to obtain a first value using diffusion-ordered spectroscopy (DOSY) as a transducer; contacting the tracer bound-first target protein with a sample; determining a diffusion coefficient for the tracer bound-first target protein after contacting the sample to obtain a second value using diffusion-ordered spectroscopy (DOSY) as a transducer; and identifying a presence of the second target protein in the sample when a change in the diffusion coefficient values is determined.

These and other features of the present subject matter will become readily apparent upon further review of the following specification.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Biosensor technology has become a major player in many applications ranging from military industries to the healthcare field. However, many challenges are facing these sectors such as detecting low-concentration protein complexes in biological samples or understanding protein properties interaction. To address these issues, the present subject matter relates to a sophisticated approach for detecting biomolecules by calculating the Diffusion rate using Diffusion Ordered Spectroscopy (DOSY) as a transducer. The developed technique enables the detection of biomaterials such as proteins and DNA by measuring the rate of diffusion coefficient before and after their interaction utilizing tracer molecules including polyfluorine. For example, the diffusion coefficient rates of biotin-pentadecafluorooctanoyl and avidin-biotin-pentadecafluorooctanoyl complex were calculated and found to be $1.937 \times 10^{-8}$ m$^2$/s and $1.12 \times 10^{-12}$ m$^2$/s respectively.

The variations in diffusion rate can be attributed to the alterations in molecular weight and size, which align with the interaction between the tracer and the target molecule. The utilization of Polyfluorine and analogous molecules as tracers can achieve precise and selective results without requiring the use of a secondary antibody or additional purification steps. Analytical methods like mass spectrometry and nuclear magnetic resonance (NMR) were employed for material characterization.

DOSY is a frequently utilized NMR technique that allows for the observation of molecular diffusion phenomena through the application of a pulse field gradient (PFG) NMR measurement approach. The DOSY technique is widely utilized for various purposes, including the separation of acylglycerol mixtures and methyl esters, analysis of the binding interactions between small ligands (such as epigallocatechin gallate) and large proteins (like salivary protein), and the identification of specific compounds within a mixture.

The present subject matter relates to preparing molecular tracers that can specifically bind to target molecules to achieve molecular interactions and converting the interactions into signals detectable using diffusion-ordered spectroscopy (DOSY) as a transducer.

In an embodiment, the present method relates to detecting molecular interactions, including avidin-biotin interactions, or other protein interactions. The avidin-biotin interaction is known to be one of the strongest non-covalent interactions in nature. Therefore, avidin and its analogs are widely used as affinity matrix probes for various applications such as diagnosis, biochemical analysis, selective purification, and biosensing.

The present subject matter relates to a method for detecting a presence of a biomolecule in a sample based on detected biomolecular interactions. The method may include preparing a molecular tracer and binding the molecular tracer to a first target protein to provide a tracer-bound first target protein. The molecular tracer may include atoms with a single spin quantum number ($\pm\frac{1}{2}$) such as, by non-limiting example, polyfluorine molecules. In other implementations, the protein may be weakly expressed. The method may include binding the tracer-bound first target protein to one or more target proteins to achieve molecular interactions. The method includes converting the interactions into signals using diffusion-ordered spectroscopy (DOSY) as a transducer. By non-limiting example, the biomolecular interactions may also include protein-protein, protein-pathogen, protein-small molecules, and gene interactions. The method can include detecting one or more biomolecules in the biomolecular interactions.

In further embodiments, the method can include determining the molecular diffusion rate of the biomolecular interactions using the DOSY. Different biomolecules such as proteins have different molecular weights and, therefore, different diffusion rates. Small molecules such as tracers could be conjugated on a desired molecule to be studied. When the tracer molecule binds to other molecules, they become slower and consequently their diffusion is reduced, confirming the interaction. This may explain the high selectivity of using these tracers in detecting molecule interactions using DOSY as a transducer.

The utilization of a polyfluorine tracer may enable protein detection without the necessity of using a secondary antibody or additional purification or separation steps. The method of the present subject matter may offer exceptional selectivity and sensitivity towards the desired target amidst a complex protein mixture which may be due to signal amplification. As a means of illustration, where every single binding event between biotin and avidin can be identified by a signal of 60 fluorine atoms and this number can be increased if the protein of interest has a low concentration. Such adaptability opens up possibilities for utilizing DOSY with live samples such as biomarkers and pathogens, eliminating the need for purification or target extraction.

In various embodiments, the molecular tracer may be bound to a first target protein. In some embodiments, the molecular tracer may be pentadecafluorooctanoyl. In an embodiment, the first target protein is biotin. In an embodiment, binding the molecular tracer to biotin to obtain a tracer-bound first target protein may include dissolving biotin hydrazide in tetrahydrofuran (THF) to obtain a reaction mixture. In various embodiments, the method may include dissolving the biotin hydrazide in at least about 5 mL THF. In other embodiments, the amount of THF may be more than 5 mL, 5 mL, or less than 5 mL. The method may include adding triethylamine to the reaction mixture to obtain a second reaction mixture and stirring the second reaction mixture for at least about 15 minutes. The method may include adding pentadecafluorooctanoyl chloride dropwise to the second reaction mixture under nitrogen gas to obtain a third reaction mixture and stirring the third reaction mixture for at least about four hours at room temperature. The method may include removing the THF from the third reaction mixture under reduced pressure to obtain a fourth reaction mixture. The method may include purifying the fourth reaction mixture and obtaining the molecular tracer. In various embodiments, the purifying may include using column chromatography with methanol and dichloromethane (DCM). In further embodiments, other forms of purification may be used. In still other embodiments, other eluents may be used in addition to or in place of methanol and DCM.

In various embodiments, the tracer-bound first target protein may be bound to a second target protein. In an embodiment, the second target protein may be avidin. In other embodiments, other proteins may be a target protein of the method of detecting biomolecular interactions. In further embodiments, avidin may be used as an affinity matrix probe. In various embodiments, the affinity matrix probe may be used in applications selected from a group consisting of diagnosis, biochemical analysis, selective purification, and biosensing.

In an embodiment, the present subject matter relates to a method of binding a molecular tracer to a first target protein. In one embodiment, the method may include dissolving biotin hydrazide in tetrahydrofuran (THF) to obtain a reaction mixture, adding triethylamine to the reaction mixture to obtain a second reaction mixture, stirring the second reaction mixture for at least about 15 minutes, adding pentadecafluorooctanoyl chloride to the second reaction mixture to obtain a third reaction mixture. In various embodiments, the pentadecafluorooctanoyl chloride may be added dropwise to the second reaction mixture. In other embodiments, the pentadecafluorooctanoyl chloride may be added to the second reaction mixture in other ways such as, by non-limiting example, pouring. In some embodiments, the second reaction mixture may be under pressure with nitrogen gas. In other embodiments, the second reaction mixture may be under pressure with another appropriate gas. The method may also include stirring the third reaction mixture. In various embodiments, stirring may last for at least about four hours, four hours, or more than four hours. In certain embodiments, the third reaction mixture may be stirred at room temperature. The method also includes removing the THF from the third reaction mixture under reduced pressure to obtain a fourth reaction mixture. The method may include purifying the fourth reaction mixture. In various embodiments, the method may include using column chromatography with methanol and dichlormethane (DCM).

In another embodiment, the molecular tracer may be used to detect proteins by binding to one or more target proteins in a sample. In various embodiments, method is not limited to detecting biomolecules. In certain embodiments, the method may be applied to various types of molecular interactions that exhibit a variation in molecular weight.

In certain embodiments, binding of the molecular tracer with the one or more target proteins is detected as a signal using diffusion-ordered spectroscopy (DOSY) as a transducer. In various embodiments, the one or more target proteins may be identifiable by the signal. The method may also include determining a molecular diffusion rate of the interaction using the DOSY.

The present subject matter relates to a technique that identifies biomolecular interactions, including protein-protein, protein-pathogen, protein-small molecules, and gene interactions. The identification of biomolecular interactions may be achieved through the utilization of empirical data gathered via diffusion-ordered spectroscopy in the detection process. Diffusion-ordered spectroscopy may enable the determination of molecular diffusion rates. An important part of this method may include preparing the tracers that may be synthesized via straightforward synthesis techniques which are derivatives of polyfluorine molecules. The tracers may refer to any molecule containing atoms with a single spin quantum number ($\pm\frac{1}{2}$) that is not a fundamental component of the tissue structure. These atoms may be unique within natural tissue molecules, such as fluorine. The detection mechanism may be based on the recognition of molecular interactions by monitoring the shift in diffusion velocity of these biomolecules prior to and following the interaction. The diffusion rate may be calculated based on the Stokes-Einstein equation and/or via the Stejskal-Tanner equation. This method may not be limited to biomolecules and can be applied to various types of molecular interactions that exhibit a variation in molecular weight.

According to an embodiment, a method of detecting a second target protein in a sample can include preparing a tracer bound-first target protein; determining a diffusion coefficient for the tracer bound-first target protein before contacting the tracer bound-first target protein with a sample to obtain a first value; contacting the tracer bound-first target protein with a sample; determining a diffusion coefficient for the tracer bound-first target protein after contacting the sample to obtain a second value; and identifying a presence of the second target protein in the sample when a change in the diffusion coefficient values is determined.

The following examples relate to various methods of manufacturing the specific compounds and application of the same, as described herein.

EXAMPLES

Materials

All chemicals and dendrimers were used as received with high purity and no need for further purification from Sigma Aldrich, such as (+)-Biotin hydrazide, 3,3,3-trifluoropropionyl chloride, Perfluorobutyryl chloride, Pentadecafluorooctanoyl chloride, poly(amidoamine) PAMAM dendrimer ethylenediamine core generation 4.0 solution, triethylamine, tetrahydrofuran (THF), avidin, phosphate-buffered saline (PBS), and buffer solution (PH=7.4). Milli-Q® grade was used in all experimental parts (18 µΩ·cm with 0.023 ppm dissolved solids, 3 ppb TOC). Mass spectroscopy technique was performed to confirm the molecular weight of the ligand, molecule, ligand-molecule interactions after binding (GC MS-DFS model TRACE GC ULTRA powered by Thermos Fisher Scientific, using Electron Impact Ionization (EI) ionization technique). Proton NMR spectra were recorded using Avance II 600 MHz (DCM), Bruker, Germany spectrometers at Kuwait University-Research Sector Project Unit (RSPU).

All synthesis steps were carried out in a laboratory using classic synthesis protocols. Thin layer chromatography (TLC) was used after each synthesis step using a 1:1 ratio from a methanol and dichloromethane mixture. In addition, for compound purification a column was used with stationary phase silica gel size (ultra-pure 40-60 µM, 60 A), and mobile phase using methanol with DCM (1:1 ratio). All reactions were done at room temperature.

All DOSY NMR spectra were recorded using Bruker 600 MHz AVANAC III NMR spectrometer equipped with Bruker BBOF probe (BrukerBioSpin, Rheinstetten, Germany). DOSY NMR Spectroscopy samples were prepared in $D_2O$ buffer at a concentration of 1 mg/mL (within the infinite dilution range for these samples at 0.1-2.1 mM). Temperatures are between 20° C. and 30° C., and samples were allowed to equilibrate for 15 minutes. $^1H$ NMR spectra were obtained prior to diffusion experiments. The DOSY gradient-compensated stimulated echo with spin lock and convection compensation (DgcsteSL_cc) pulse sequence was used with a diffusion gradient length of 4.0 ms and a diffusion delay of 200 ms. A 10 s relaxation delay was employed with a total of 16 scans. For analysis, the entire spectral region from 3.7 to 2.3 ppm was used and arbitrarily set to an integral value of 100 for the gradient eld strength (G) of 0 G/cm for each sample.

Tetramethyl silane (TMS) was used as an internal chemical shift reference, where the signal was set at 0.0 ppm to correct chemical shifts. Before Fourier treatment, the FID signals were amplified by an exponential line-Broadening factor of 1 Hz. The spectrum was manually phased, and the baseline was automatically adjusted using the "abs n" command. The $^{19}F$ NMR spectra were recorded using Pulse Sequence (zgflqn) program from Bruker pulse standard library. The spectral width was set to 600 ppm digitized to 132 k data point; the number of scans was 1-4 k with a 4 second recycle delay. 2D spectra were measured using double stimulated echo and LED using 3 spoil gradients. The diffusion time was optimized to 200 ms with gradient pulse 2000 us. Bruker Topspins3.5p17 (BrukerBioSpin, Rheinstetten, Germany) was used for both data collection and spectral processing.

Example 1

Synthesis of Avidin-Biotin Complex (+)-Biotin hydrazide (100 mg, 0.3870 m-mol) was dissolved in 5 mL tetrahydrofuran (THF). Triethylamine (58.75 mg, 0.5806 mmol) was added to the solution and the reaction mixture was left to stir for 15 minutes at room temperature. Pentadecafluorooctanoyl chloride (200.90 mg, 0.4645 mmol) was added dropwise to the solution under nitrogen gas. The mixture was then allowed to stir for 4 hours at room temperature. After completion, THF was removed under reduced pressure and the obtained mixture was purified by column chromatography using methanol and dichloromethane DCM (1:1 ratio) to obtain the avidin-biotin complex with 77.2% yield.

$^1$H-NMR (600 MHz, DMSO), 10.86 (S, 2×NH—CO), 10.08 (S, 2×NH), 4.50 (T, CH), 4.60 (Q, CH), 3.10-2.85 (D, $CH_2$—S), 3.27 (Q, $CH_2S$—CH—$CH_2$), 1.58 (Q, CH—$CH_2$—$CH_2$), 1.25 (Quin, 2×$CH_2$—$CH_2$—$CH_2$), 2.19 (T, $CH_2$—$CH_2$—CO). $^{13}$C-NMR (600 MHz, DMSO), 164.7 (S, CO—NH), 62.5 (S, 2×CH), 41.1 (S, $CH_2$—S), 55.6 (S, $CH_2S$—CH—$CH_2$), 24.8 (S, CH—$CH_2$—$CH_2$), 29.2 (S, 2× $CH_2$—$CH_2$—$CH_2$), 38.2 (S, $CH_2$—$CH_2$—CO), 176.6 (S, CO—NH), 174.1 (S, CO—$CF_2$), 177.3 (S, CO—$CH_2$), 46.2 (S, $CH_2$—$CF_3$), 109.3 (S, $CF_3$). m/z GC-MS (EI) calculated $C_{18}H_{17}F_{15}N_4O_3S$: 654.40, Found: 654.59.

PAMAM dendrimer ethylenediamine core generation 4.0 solution (81.3 mg, 5.72×10$^{-3}$ mmol) was added in round flask and mixed with pentadecafluorooctanoyl chloride (158.32 mg, 0.366 mmol) dropwise under nitrogen gas (Scheme S1). The mixture was then allowed to stir for 7 hours at room temperature. $^1$H-NMR (400 MHz, CDCL$_3$), 4.02 (T, NH), 3.48 (T, NH$_2$), 1.93 (T, CH$_2$—CO), 1.72 (Q, CH$_2$—NH), 1.69 (Quin, CH$_2$—NH$_2$), 1.35 (T, CH$_2$—CH$_2$—N). m/z MALDI-TOF MS calculated [NH$_2$(CH$_2$)$_2$NH$_2$]: (G=4); dendri PAMAM(NHCOCF$_2$(CF$_2$)$_5$CF$_3$)$_{64}$]: 40588.57, Found: 40550.09.

Following any of the above synthesis, 1.5 mL of phosphate-deuterated buffered saline (PH=7.4) was added to each sample, and the samples were sonicated to ensure their solvation in the buffer solution (H$_2$O was replaced D$_2$O). This step was done for 2 minutes using an ultrasonicator device (OMNI RUPTOR 4000) at 20 Watts. Then the prepared solution was mixed with 1 M NaCl, 10 mM EDTA, $4 \times 10^{-9}$ mol avidin with solutions of bovine serum albumin ($10^{-8}$ mol) as an excess (H$_2$O was replaced D$_2$O) to form a new stock solution. Subsequently, 100 µL was taken from the stock solution and combined with 0.5 mL of D$_2$O. Then the samples were tested and studied by NMR technique.

Example 2

Diffusion Coefficient Determination in DOSY

A monoexponential fit of the decay signal for each peak to the Stejskal-Tanner equation (Equation 1, below) gives the associated diffusion coefficient D. The resonances can then be sorted according to the value of the diffusion coefficient. Diffusion encoding experiments can be added or appended to many nD spectroscopy experiments. Appropriate data processing then produces an (n+1) D spectrum with n chemical shift axes and an additional diffusion axis. In a classic two-dimensional DOSY display, the first dimension corresponds to the one-dimensional NMR spectrum of the sample and the second dimension corresponds to the diffusion coefficient; peaks of the same molecule are aligned along corresponding values of the diffusion coefficient. The data processing methods of DOSY can be divided into univariate and multivariate methods, many of which are implemented in the open DOSY Toolbox and recently extended to GNAT, which greatly facilitates the analysis of DOSY data.

$$I = I_0 e^{-\gamma^2 \delta^2 G^2 \left(\Delta - \frac{\delta}{3}\right) D},\qquad \text{Equation 1}$$

Example 3

Avidin-Biotin Pentadecafluorooctanoyl

In general, biotin-labeled molecules [N'-(2,2,3,3,4,4,4-heptafluorobutanoyl)-5-((3aS,4S,6aR)-2-oxohexahydro-1H-thieno[3,4-d]imidazol-4-yl)pentanehydrazide] were prepared by covalently coupling the pentadecafluorooctanoyl to the biotin via a one-step reaction (Schotten Baumann reaction) where the amide was synthesized from acyl chloride (perfluoro-butyryl) and amine (biotin) interaction. Using a base-catalyst (triethyl amine) is vital to neutralize the hydrochloric acid bi-product formed during the reaction that inhibits the back reaction. The noncovalent immunological conjugation step was performed using classic biotin-avidin incubation protocol. Biotin-pentadecafluorooctanoyl was incubated with avidin (1 M NaCl, 10 mM EDTA, $4 \cdot 10^{-9}$ mol avidin and $10^{-8}$ mol bovine serum albumin (excess). Avidin has four identical subunits, each one contains one binding site for biotin. Once a small and stable labeled biotin is added, a rapid non-covalent interaction between avidin and biotin will occur due to the high affinity of this system. Typically, avidin and biotin-pentadecafluorooctanoyl are mixed in a specific ratio to avoid avidin saturation. Then the mixture was incubated at room temperature for 1 hour to form the complex of interest and then stored at 4° C.

Three tracer compounds, A (Scheme 1), B (Scheme 2) and C (Scheme 3) with a different number of fluorine chains were synthesized. Compounds A and B did not give satisfying results in terms of signal intensity due to the short length of the fluorine chain. Therefore, the optimum tracer was compound C. Fluorine was used on the tracers because it would not interfere with $^1$H-NMR signal, and it is naturally not available in organic compounds.

Example 4

Synthesis of Compound A (+)-Biotin hydrazide (100 mg, 0.3870 m-mol) was dissolved in 5 mL tetrahydrofuran (THF). Triethylamine (58.75 mg, 0.5806 mmol) was then added to the solution, and the reaction mixture was left to stir for 15 minutes at room temperature. Perfluorobutyryl chloride (107.99 mg, 0.4645 mmol) was added dropwise to the solution under the presence of nitrogen gas. The mixture was then allowed to stir for about four hours at room temperature. After completion, THF was removed under reduced pressure and a crude mixture was obtained. The mixture was purified by column chromatography using methanol and DCM (1:1 ratio) to render the desired product (compound A) with 82.1% yield.

(+)-Biotin hydrazide

Perfluorobutyryl chloride compound A

Scheme 1. Synthesis Scheme of Compound A

N'-(2,2,3,3,4,4,4-heptafluorobutanoyl)-5-((3aS,4S,6aR)-2-oxohexahydro-1H-thieno[3,4-d]imidazol-4-yl)pentanehydrazide

Example 5

Synthesis of Compound B (+)-Biotin hydrazide (100 mg, 0.3870 m-mol) was dissolved in 5 mL tetrahydrofuran (THF). Triethylamine (58.75 mg, 0.5806 mmol) was then added to the solution and the reaction mixture was left to stir for 15 minutes at room temperature. 3,3,3-trifluoropropionyl chloride (68.05 mg, 0.4645 mmol) was added dropwise to the reaction mixture under nitrogen gas. The mixture was then allowed to stir for about four hours at room temperature. THF was removed under reduced pressure and the obtained mixture was then purified by column chromatography using methanol and DCM (1:1 ratio) to receive the desired product (compound B) with 85.05% yield.

Synthesis of Compound B

Scheme 2. Synthesis Scheme of Compound B

5-((3aS,4S,6aR)-2-oxohexahydro-1H-thieno[3,4-d]imidazol-4-yl)-N'-(3,3,3-trifluoropropanoyl)pentanehydrazide

Example 6

Synthesis of Compound C (+)-Biotin hydrazide (100 mg, 0.3870 m-mol) was dissolved in 5 mL tetrahydrofuran (THF). Triethylamine (58.75 mg, 0.5806 mmol) was added to the solution and the reaction mixture was left to stir for 15 minutes at room temperature. Pentadecafluorooctanoyl chloride (200.90 mg, 0.4645 mmol) was added dropwise to the solution under nitrogen gas. The mixture was then allowed to stir for four hours at room temperature. After completion, THF was removed under reduced pressure and the obtained mixture was purified by column chromatography using methanol and DCM (1:1 ratio) to obtain the desired product (compound C) with 77.2% yield.

Synthesis of Compound C

Scheme 3. Synthesis of Compound C 2,2,3,3,4,4,5,5,6,6,7,7,8,8,8-pentadecafluoro-N'-(5-((3aS,4S,6aR)-2-oxohexahydro-1H-thieno[3,4-d]imidazol-4-yl)pentanoyl)octanohydrazide The Stejskal-Tanner equation (Equation 1) was utilized to compute the diffusion coefficient of the tracer biotin-pentadecafluorooctanoyl before interaction with avidin, as well as the avidin-biotin-pentadecafluorooctanoyl complex, providing a quantitative illustration of the signal intensity.

$$I = I_0 e^{-\gamma 2 \delta 2 G^2 (\Delta - \delta/3) D} \tag{Equation 1}$$

Where (I) is the intensity, ($I_0$) is the intensity without gradient, ($\gamma$) is the gyromagnetic ratio, ($\delta$) is the gradient pulse duration, which is kept constant during the experiment, (G) is the gradient strength which kept changing during the experiment, ($\Delta$) is the delay (diffusion time), and (D) is the diffusion coefficient which can be extracted easily.

Upon implementing the experimental values into Equation 1, the diffusion coefficient for the biotin-pentadecafluorooctanoyl and avidin-biotin-pentadecafluorooctanoyl complex was successfully determined. The calculated values were $1.937 \times 10^{-8}$ m²/s and $1.12 \times 10^{-12}$ m²/s respectively. Upon comparing these two values, a significant difference of four orders of magnitude in the diffusion coefficients of the two molecules was observed. This discrepancy can be attributed to the transition from simple biotin-pentadecafluorooctanoyl to the larger complex avidin-biotin-pentadecafluorooctanoyl during the interaction process. The change in the diffusion coefficient serves as an indication of the tracer's ability to selectively detect the presence of the avidin protein in a mixture, even among other proteins, utilizing these Polyfluorine tracers.

Different molecules such as proteins have different molecular weights and, therefore, different diffusion rates. Small molecules such as tracers could be conjugated on a desired molecule to be studied. When the tracer molecule binds to other molecules, they become slower and consequently their diffusion is reduced, confirming the interaction. This explains the high selectivity of using these tracers in detecting molecule interactions using DOSY as a transducer.

The utilization of a Polyfluorine tracer enables protein detection without the necessity of a secondary antibody or additional purification or separation steps. This method offers exceptional selectivity and sensitivity towards the desired target amidst a complex protein mixture, thanks to signal amplification. Where every single binding event between biotin and avidin can be identified by signal of 60 fluorine atom and this number can be increased if the protein of interest has a low concentration. Such adaptability opens up possibilities for utilizing DOSY with live samples such as biomarkers and pathogens, eliminating the need for purification or target extraction.

According to Stokes-Einstein equation mentioned below, the diffusion coefficient of solutes is directly linked to the hydrodynamic radius.

$$R_h = \frac{k_B T}{6\pi \eta D}, \quad \text{Equation 2}$$

Where $R_h$ is the hydrodynamic radius, $k_B$ is the Boltzmann constant, T is the temperature in K and $\eta$ is the solution viscosity (~9.7 cP for $D_2O$, and 30° C.) and D is the diffusion coefficient. The diffusion coefficient value is directly proportional to the temperature (T) and inversely proportional to the hydrodynamic radius. Thus, the hydrodynamic radius is related to the molecular weight, the higher the molecular weight, the larger the radius, the lower the diffusion and vice versa.

Figure 4A:
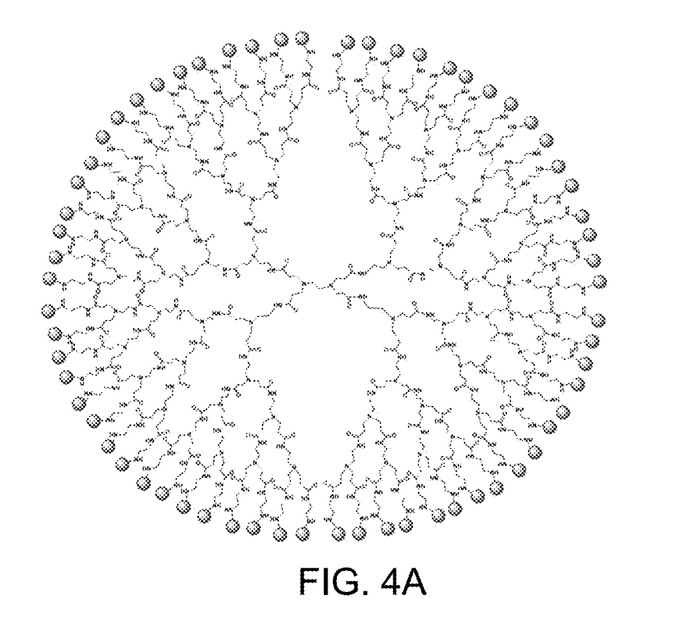
FIG. 4A shows an implementation of a structure of [NH$_2$(CH$_2$)$_2$NH$_2$]: (G=4); dendri PAMAM (NHCOCF$_2$(CF$_2$)$_5$CF$_3$)$_{64}$] (PAMAM-Polyfluorine).
Figure 4B:
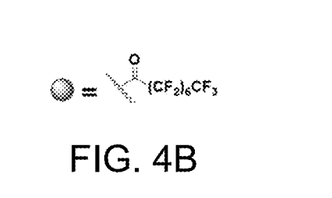
FIG. 4B shows a key for each of the balls shown in FIG. 4A.

The hydrodynamic radius ($R_h$) of avidin obtained using Equation 2 is 22.02 Å. This is similar to the measured dynamic light scattering (DLS) for aqueous native avidin (26.4±0.3 Å). This indicates the accuracy of this method to determine these types of structural parameters. This tool could prove to further validate the use of Stokes-Einstein equation of calculating the hydrodynamic radius. The hydrodynamic radius of the newly synthesized PAMAM-Polyfluorine (FIGS. 4A and 4B) was compared to the commercially available PAMAM (G=4). The obtained results were 4.3 nm and 2.8 nm respectively. The PAMAM hydrodynamic radius is in good agreement with that of PAMAM measured by Transmission electron microscopy (TEM). This shows the precision of the method for determining such structural parameters.

Figure 1:
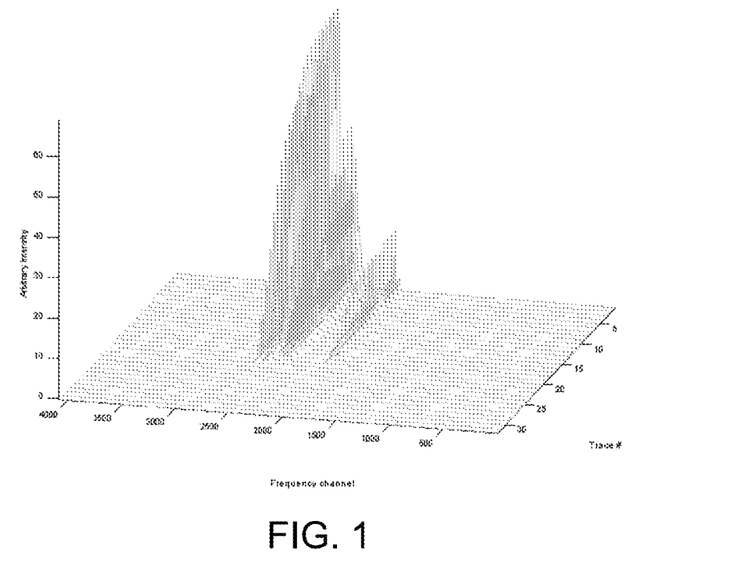
FIG. 1 shows an arrayed diffusion-ordered spectroscopy (DOSY) spectra of PAMAM in an implementation of the method as described herein.
Figure 2:
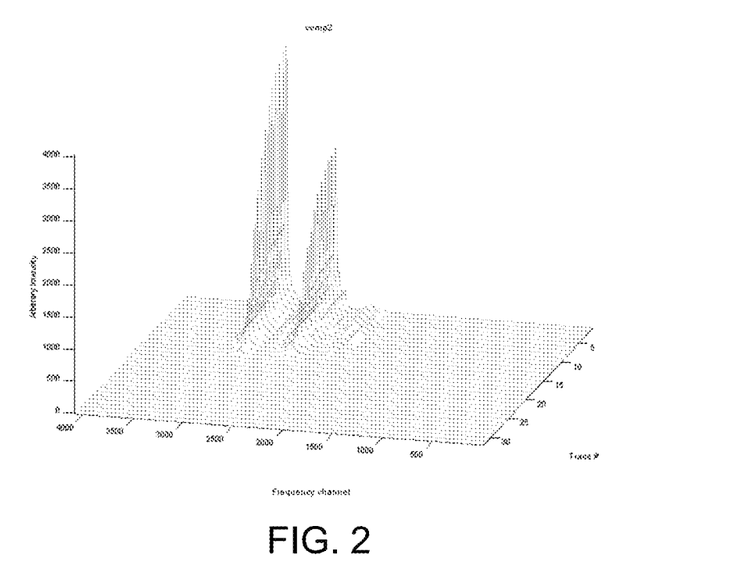
FIG. 2 shows an arrayed DOSY spectra of poly(amidoamine) (PAMAM)-polyfluorine in an implementation of the method as described herein.

The diffusion coefficients (D) and hydrodynamic radius ($R_h$) of the isolated product from the PAMAM-Polyfluorine conjugation were examined using DOSY. It is well known that larger structures diffuse slowly compared to smaller molecules, which can be detected by the spin-echo signal changes caused by the special displacement distribution of the nuclei resonant in a magnetic field with nuclear magnetic relaxation processes and gradient. Empirically, a shift in the rate of decay signal in a pulse field gradient experiment is observed (FIGS. 1 and 2).

After rearranging Equation 1, the following equation is obtained:

$$\ln\left(\frac{I}{I_0}\right) = -\gamma^2 \delta^2 G^2 \left(\Delta - \frac{\delta}{3}\right) D, \quad \text{Equation 3}$$

Figure 3:
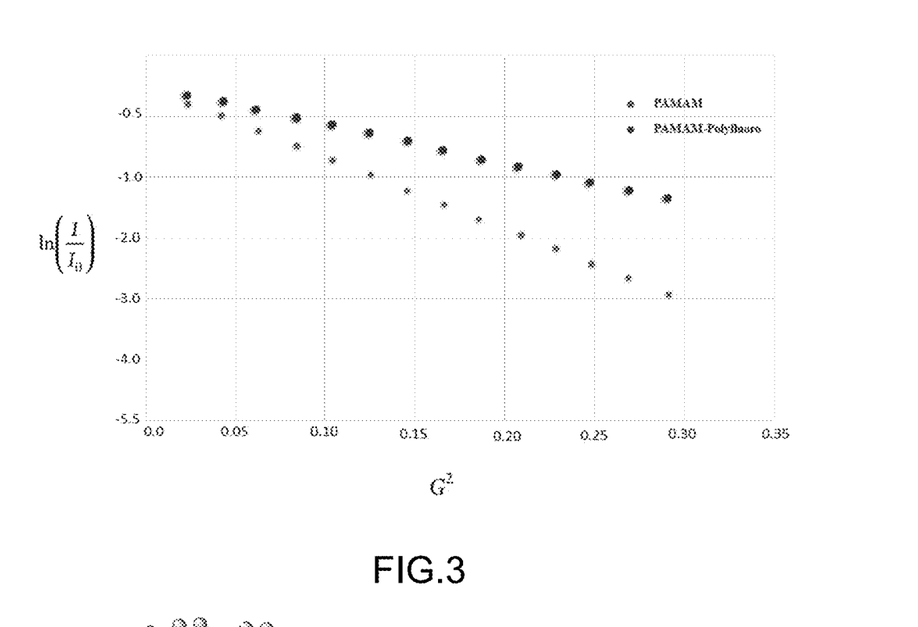
FIG. 3 shows a Stejskal-Tanner plot of PAMAM-NH$_2$ in an implementation of the method as described herein; with PAMAM shown as the bottom line of dots and PAMAM-Polyfluorine shown as the top line of dots.

Now, equation 3 is a linear equation. The diffusion coefficient can be calculated by finding the slope.

Where G is the gradient field strength (in Gauss/cm), I is the integral of the peak area at a given value G, $I_0$ is the integral of the peak area at G=0, $\gamma$ is the gyromagnetic ratio of the nucleus ($2.675\times10^8$ $T^{-1}$ $s^{-1}$ for 1H), $\delta$ is the diffusion gradient length parameter (4.0 ms), $\Delta$ is the delay (diffusion time) (100.0 ms), and D is the diffusion coefficient. The Stejskal-Tanner plots of PAMAM-NH2 G=4 with and without Polyfluorine, are shown in FIG. 3, where alkylic proton signal at 2.4 ppm.

According to the Stokes-Einstein equation (Equation 2), the diffusion coefficient (D) has an inversely proportional relationship with hydrodynamic radius ($R_h$). This complies very well with the acquired results. The diffusion coefficients of PAMAM (Mm=14215 g/mol) and PAMAM-Polyfluorine (Mm=40550 g/mol) are $1.8\times10^{10}$ $m^2/s$ and $0.74\times10^{10}$ $m^2/s$ respectively. The diffusion coefficient dropped to more than half when the conjugation between PAMAM and Polyfluorine took place. On the other hand, the hydrodynamic radius increased from 2.8 nm in PAMAM to 4.3 nm in PAMAM-Polyfluorine confirming the PAMAM and Polyfluorine conjugation.

It is to be understood that the method to detect a biomolecule based on a diffusion coefficient rate of a biomolecular interaction are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method for detecting a presence of a second target biomolecule in a sample, the method comprising:
   preparing a molecular tracer;
   binding the molecular tracer to a first target biomolecule to provide a tracer bound-first target biomolecule;
   contacting the tracer bound-first target biomolecule with the sample;
   determining a first diffusion coefficient value for the tracer bound-first target biomolecule before contacting the tracer bound first-target biomolecule with the sample;
   determining a second diffusion coefficient value for the tracer bound-first target biomolecule after contacting the tracer bound-first target biomolecule with the sample; and
   determining difference in diffusion coefficient values between the first and the second diffusion coefficient values, wherein detecting a change of four orders of magnitude in the diffusion coefficient values indicates binding of the second target biomolecule with the tracer bound-first target biomolecule, thereby detecting the presence of the second target biomolecule in the sample;

wherein the molecular tracer comprises pentadecafluorooctanoyl; and wherein the first target biomolecule is biotin; and wherein the second target biomolecule is avidin.

2. The method of claim 1, wherein providing a tracer bound-first target biomolecule comprises:
dissolving biotin hydrazide in 5 mL tetrahydrofuran (THF) to obtain a reaction mixture;
adding triethylamine to the reaction mixture to obtain a second reaction mixture;
stirring the second reaction mixture for at least about 15 minutes;
adding pentadecafluorooctanoyl chloride dropwise to the second reaction mixture under nitrogen gas to obtain a third reaction mixture;
stirring the third reaction mixture for at least about four hours at room temperature;
removing the THF from the third reaction mixture under reduced pressure to obtain a fourth reaction mixture; and
purifying the fourth reaction mixture using column chromatography with methanol and dichloromethane (DCM).

3. The method of claim 1, wherein the avidin is used as an affinity matrix probe.

4. The method of claim 1, wherein the affinity matrix probe is used in applications selected from a group consisting of diagnosis, biochemical analysis, selective purification, and biosensing.

5. A method of detecting a second target biomolecule in a sample, comprising:
preparing a tracer bound-first target biomolecule;
determining a diffusion coefficient for the tracer bound-first target biomolecule before contacting the tracer bound-first target biomolecule with the sample to obtain a first diffusion coefficient value using diffusion-ordered spectroscopy (DOSY) as a transducer;
contacting the tracer bound-first target biomolecule with the sample;
determining a diffusion coefficient for the tracer bound-first target biomolecule after contacting the sample to obtain a second diffusion coefficient value using diffusion-ordered spectroscopy (DOSY) as a transducer;
determining difference in the diffusion coefficient values between the first diffusion coefficient value and the second diffusion coefficient value; and
identifying the presence of the second target biomolecule in the sample when the determined difference in the diffusion coefficient values is of four orders of magnitude, whereby the change in the diffusion coefficient values indicates a binding of the second target molecule with the tracer-bound first target biomolecule;
wherein the tracer is pentadecafluorooctanoyl; and
wherein the first target biomolecule is biotin and the second target biomolecule is avidin.

6. The method of claim 5, wherein the tracer bound-first target biomolecule is prepared by:
dissolving biotin hydrazide in 5 mL tetrahydrofuran (THF) to obtain a reaction mixture,
adding triethylamine to the reaction mixture to obtain a second reaction mixture,
stirring the second reaction mixture for at least about 15 minutes,
adding pentadecafluorooctanoyl chloride dropwise to the second reaction mixture under nitrogen gas to obtain a third reaction mixture,
stirring the third reaction mixture for at least about four hours at room temperature,
removing the THF from the third reaction mixture under reduced pressure to obtain a fourth reaction mixture, and
purifying the fourth reaction mixture using column chromatography with methanol and dichloromethane (DCM) to provide the tracer bound first target biomolecule.

* * * * *